United States Patent
Napper et al.

(10) Patent No.: US 7,485,217 B2
(45) Date of Patent: Feb. 3, 2009

(54) DENTAL INSTRUMENT CLEANSING APPARATUS

(75) Inventors: David Napper, Aabenraa (DK); Henry Lund Pedersen, Kolding (DK); Lene Rubner-Petersen, Give (DK)

(73) Assignee: Adept Water Technologies A/S, Vebbaek (DK)

( * ) Notice: Subject to any disclaimer, the term of this patent is extended or adjusted under 35 U.S.C. 154(b) by 254 days.

(21) Appl. No.: 10/529,042

(22) PCT Filed: Sep. 26, 2003

(86) PCT No.: PCT/EP03/10728

§ 371 (c)(1),
(2), (4) Date: Apr. 4, 2006

(87) PCT Pub. No.: WO2004/028392

PCT Pub. Date: Apr. 8, 2004

(65) Prior Publication Data

US 2006/0191823 A1     Aug. 31, 2006

(30) Foreign Application Priority Data

Sep. 27, 2002    (EP) .................................. 02256747

(51) Int. Cl.
*A61C 1/00*     (2006.01)
(52) U.S. Cl. .......................... 210/97; 210/138; 210/143

(58) Field of Classification Search .................. 210/97, 210/138, 143; 422/105
See application file for complete search history.

(56) References Cited

U.S. PATENT DOCUMENTS

| 5,709,546 A | 1/1998 | Waggoner |
| 6,773,610 B2 * | 8/2004 | Korin .......................... 210/748 |

FOREIGN PATENT DOCUMENTS

| EP | 0233847 A | 8/1987 |
| WO | WO 96/29098 A | 9/1996 |

* cited by examiner

*Primary Examiner*—Terry K Cecil
(74) *Attorney, Agent, or Firm*—Welsh & Flaxman LLC

(57) ABSTRACT

A dental unit water line (DUWL) monitoring and maintenance apparatus, for monitoring a DUWL. The apparatus has a cleansing unit attached to the DUWL for cleansing the fluid passing there through. A control unit controls the cleansing unit associated with the water line. A monitoring unit monitors the operation of the dental unit when used by a dentist and stores data related to that operation. A timer times and records data relating to both periods of dental unit activity and inactivity, wherein, in use, the control unit operates to receive data from the monitoring unit and the timer and, based upon that data and reference data controls the operation of the water line to control flow of fluid through that DUWL and controls the cleanser to control the overall cleansing procedures associated with both the dental unit and associated DUWL.

20 Claims, 4 Drawing Sheets

Level 0: maintenance - intermittent current/no current
Level n: different times and currents

DENTAL INSTRUMENT CLEANSING APPARATUS

This invention relates to a device for keeping equipment used in dental procedures clean and, more particularly, to a device for ensuring that such equipment can supply fluids for use in such procedures that are free from biological contamination, including bacteria, viruses, algae, protozoa (such as amoeba), nematodes, fungus and other smaller organisms including larva stages of both pathogenic and non pathogenic organisms.

Dentists use a variety of tools whilst performing procedures, including surgery, on patients' teeth and related facial structures. Such tools are, by their nature, expensive, so they are re-used numerous times with the dentist carrying out a cleansing operation between each procedure. Furthermore, during such dental procedures it is often necessary to provide cleaning liquid, in the form of tap water, distilled water or a water-based solution, to remove blood and other matter during those procedures, to cool patients' teeth and also in order to keep the relevant tools clean. Such fluid is usually supplied via a dental unit water line (DUWL).

However, the quality of the fluid supplied is very much dependent upon the quality of the maintenance of the tools and the associated equipment, as well as the water line itself, and this varies considerably from dentist to dentist. Furthermore, the quality of the fluid entering the unit, usually from the public water system, affects the cleanliness of the fluid supplied.

Many of the tools that are used are small, with narrow passageways passing therethrough. Also, public water supplies by definition can contain a notable number of bacteria and other organic contaminants such as algae, and the bacteria and other organic contaminants in the water have the opportunity to multiply to unacceptable levels when the water stands still in the DUWL either between patients, overnight, during weekends or vacation. Further, the bacteria can use normal constituents of water such as calcium deposits to build biofilm, which is difficult to combat once formed. Given all of this, the applicants have found that, even with optimum maintenance and rigorous checking and cleansing of the tools and their associated cleansing system and water lines, it is possible for contamination to build up and the fluid supplied to a patient via such tools to be contaminated.

According to legislation in many countries the levels of bacteria in the water going into a patients mouth may not exceed the level, specified as drinking water quality. In practice this legislation is not observed.

Another problem in the DUWL that needs to be addressed is that of mineral ions in the water lines. These convert to compounds such as calcium hydroxide and magnesium carbonate and are deposited on the walls of the DUWL. Deposits in tubes, valves, passageways and expensive instruments making up the DUWL are a problem. Previously efforts have been made to soften water with an ion exchange unit to remove mineral ions before using the water. However, the resins traditionally used to soften the water are very good growing media for bacteria, which use them to build biofilm as mentioned above, so eliminating mineral deposits increases bacterial problems. Therefore, combining an ion exchange unit with the system of the present invention solves many problems.

The present invention seeks to improve the cleanliness of the equipment and fluids used and supplied in dental procedures and hence to improve the overall level of cleanliness of the procedures themselves.

According to the present invention there is provided a dental unit water line (DUWL) monitoring and maintenance apparatus comprising:

cleansing means attached to the DUWL for cleansing the fluid passing therethrough;

control means for controlling the cleansing means of the water line;

monitoring means for monitoring the operation of the dental unit by a dentist in use and storing data related to that operation; and a timer for timing and recording data relating to both periods of dental unit activity and inactivity, wherein, in use, the control means operates to receive data from the monitoring means and the timer and, based upon that data and reference data controls the operation of the pump associated with the water line to control flow of fluid through that DUWL and controls the cleanser to control the overall cleansing procedures associated with both the dental unit and associated DUWL.

The monitoring means may monitor the types of tools being used by the dentist and which are associated with the dental unit. The monitoring means may also provide data related to the duration of use of each of those tools.

The control unit may monitor the operation of the cleansing unit to determine the level of any cleansing fluid being used by the cleansing unit. If the cleansing unit comprises an electrochemical device then the control unit may monitor the output of that device to determine when electrodes associated with that device need replacement. The control unit may be configured to provide an audio or visual warning to the dentist should any feature of the dental unit be determined to be operating incorrectly or if it is determined that any specific non-routine maintenance procedure is required. The control unit may be configured to prevent operation of the flow of liquid unless a certain sequence of maintenance procedures are first implemented by a user.

With the device of the present invention the cleansing operation of the dental unit and its associated DUWL can be controlled automatically in order to ensure regular and adequate maintenance and prevent inadvertent contamination that might be passed on either to the dentist or a patient during operation of the dental unit. Furthermore, it can ensure that appropriate maintenance of the unit is performed, as well as ensuring that tools are replaced where appropriate and that any cleansing unit is operating correctly.

An example of the present invention will now be described with reference to the accompanying drawings, in which.

Figure 1:
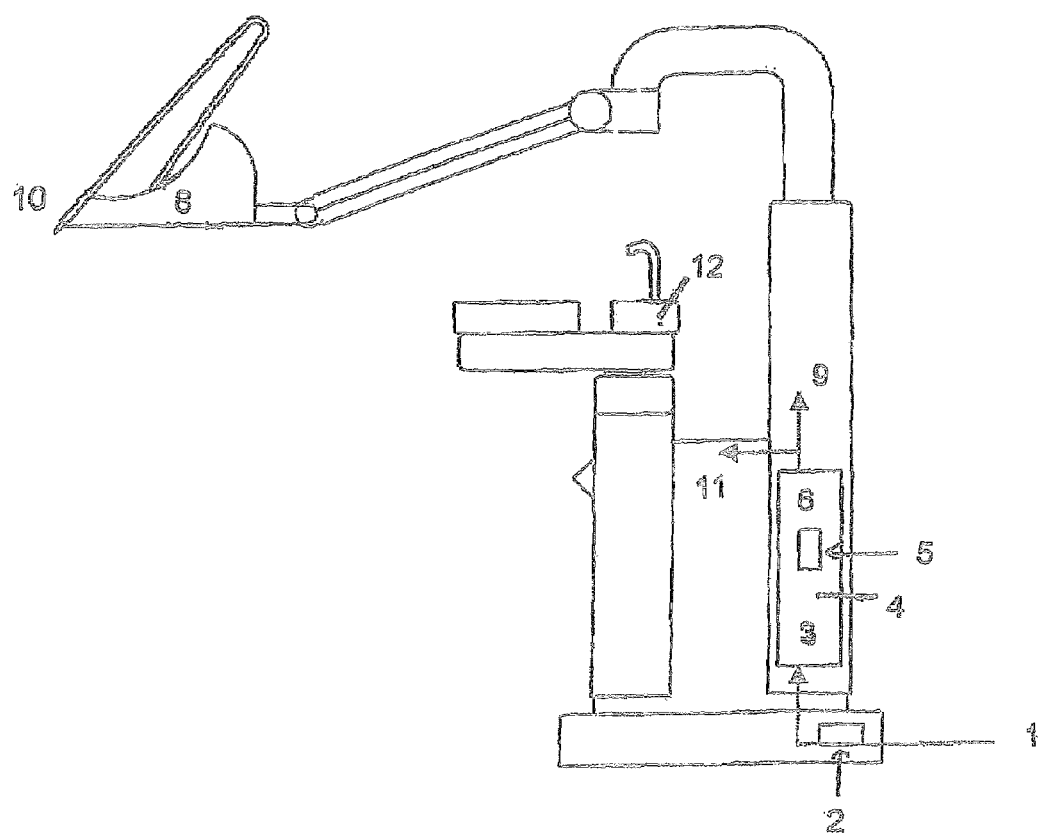
FIG. 1 is a schematic diagram showing a dental unit and cleansing and monitoring apparatus according to the present invention.

FIG. 1 shows a cleansing and monitoring apparatus according to the invention which, in use, is positioned next to a dental chair. The cleansing and monitoring apparatus has a water intake 1 that is attached, in use, to a main supply of water, or alternatively, a tank of distilled water. The apparatus has an optional ion exchange water cleansing apparatus 2 through which water from the water intake 1 passes. The output of the ion exchange unit 2 is fed through a water supply monitoring unit 3 which is coupled to a flow signal generator 4 and integral processor 6 and electrochemical device 8. Signals from the flow signal generator 4, the monitoring unit 3 and the timer 5 are fed to a central processor 6 (FIG. 2)

which provides control signals and power supply to the electrochemical device 8 and provides control of pump 9. Water is then fed out from the electrochemical device 8. The unit also has an optional water cup filler 12 and cup holder and is also connected to hand instruments 11. The processor 6 (FIG. 2) can receive operating signals from these to assist in control of flow of the water through the overall unit, as well as control of the electrochemical device 8. In use, water is passed out from the device 8 and to the cup filler 12 and hand instruments 11 on the basis of detected signals and the requests of an operator.

Figure 2:
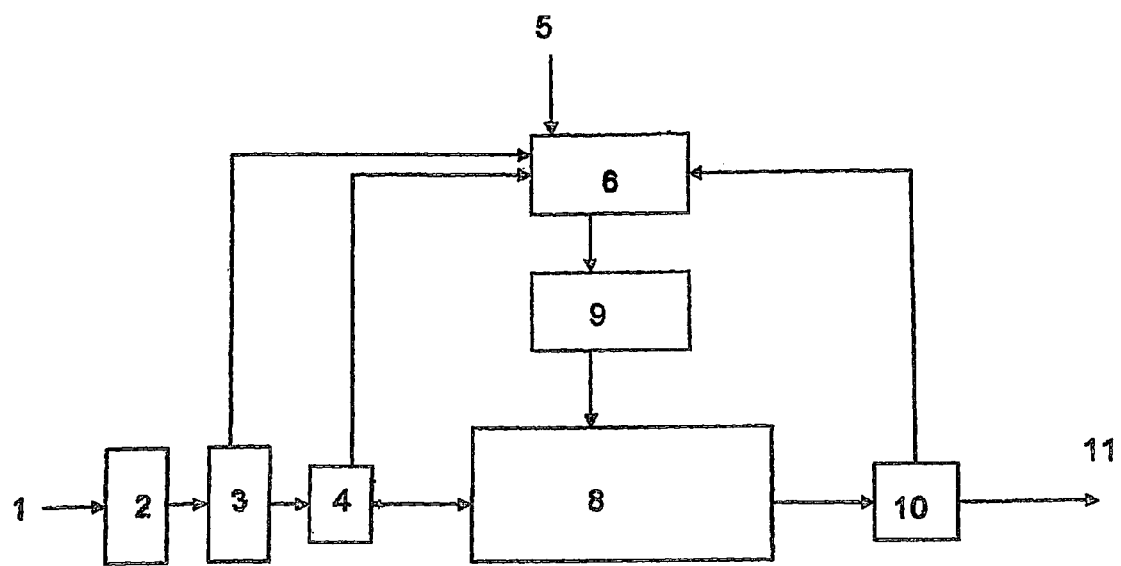
FIG. 2 is a schematic block-diagram showing the key operating components of the apparatus of the present invention.

Referring to FIG. 2, a schematic block diagram of a DUWL monitoring and maintenance apparatus with an ion exchange unit 2 is shown. This is positioned directly after the input 1 to the apparatus through which water supplied from, for example, the public water supply, is input. The ion exchange unit 2 removes mineral ions present in the water before the water enters the rest of the apparatus.

The water flows through the ion exchange unit 2 and then through the water supply monitoring unit 3 which monitors the state of water entering the rest of apparatus. Information obtained by the water supply monitoring unit 3 is sent to the processor 6 and also to the flow signal generator 4.

The water is cleansed by means of the electrochemical device 8 which receives information from the flow signal generator 4 and the processor 6 to enable an optimum cleaning process to take place.

After the water is cleansed it is further monitored by the water monitoring unit 10 before the water reaches the patient. Information from the water monitoring unit 10 is fed back to the processor 6.

The processor 6 therefore has information from monitoring of the water before and after it is cleansed and it also receives control signals from the dental unit components 11, 12. This combination of information enables an accurate analysis to be made of the type, strength and length of cleansing that is needed and the cleansing can be adjusted as necessary as the information received by the processor 6 changes.

Some of the functionality of the apparatus invention will now be described with reference to FIGS. 3A and 3B.

Figure 3A:
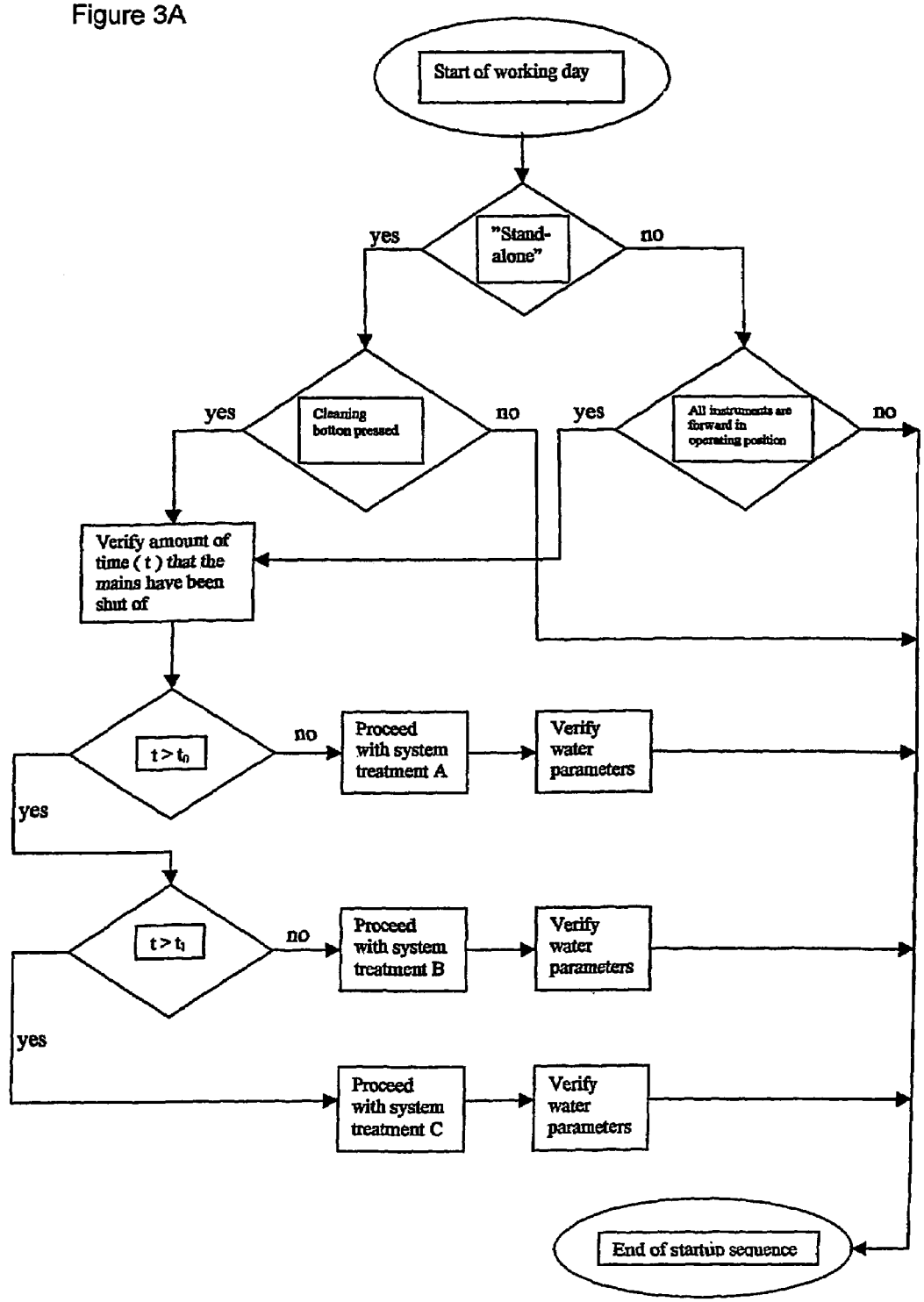
FIGS. 3A and 3B are flow charts showing some of the basic operations of the apparatus of the present invention.

FIG. 3A shows a start up procedure for the device of the present invention. At the start of the day the control unit determines whether or not the device linked to the water line is in a "stand alone" state. If it is not then it is determined whether or not the instruments associated with the line are in an operating position, and if they are not the start up sequence is not actually initiated. If they are then the system moves into a time verification step that will be described below.

If the unit is not "stand alone" then it is determined whether or not a request for cleaning has been made via a cleaning button. If no request has been made then the cleaning sequence ends, again, before it has started. If it has, then a time verification step is performed to determine how long the mains electrical supply to the device has been switched off. If it is only a short period of time, which period of time is dependent upon the type of device and its overall operation, then a first, usually very low scale, cleansing procedure is initiated, followed by a verification of the quality of the water following the cleansing operation. If the period is greater than the first time period then a second treatment procedure, again, followed by a water verification step, is performed. If it is determined that the unit has been switched off for an extended period, then an extensive cleansing procedure is performed followed by water verification. It will, of course, be appreciated that the number of individual ranges of shut-down time periods can be varied dependent upon the dental unit to which the device is attached in use and the likely extent of use of that dental unit.

Figure 3B:
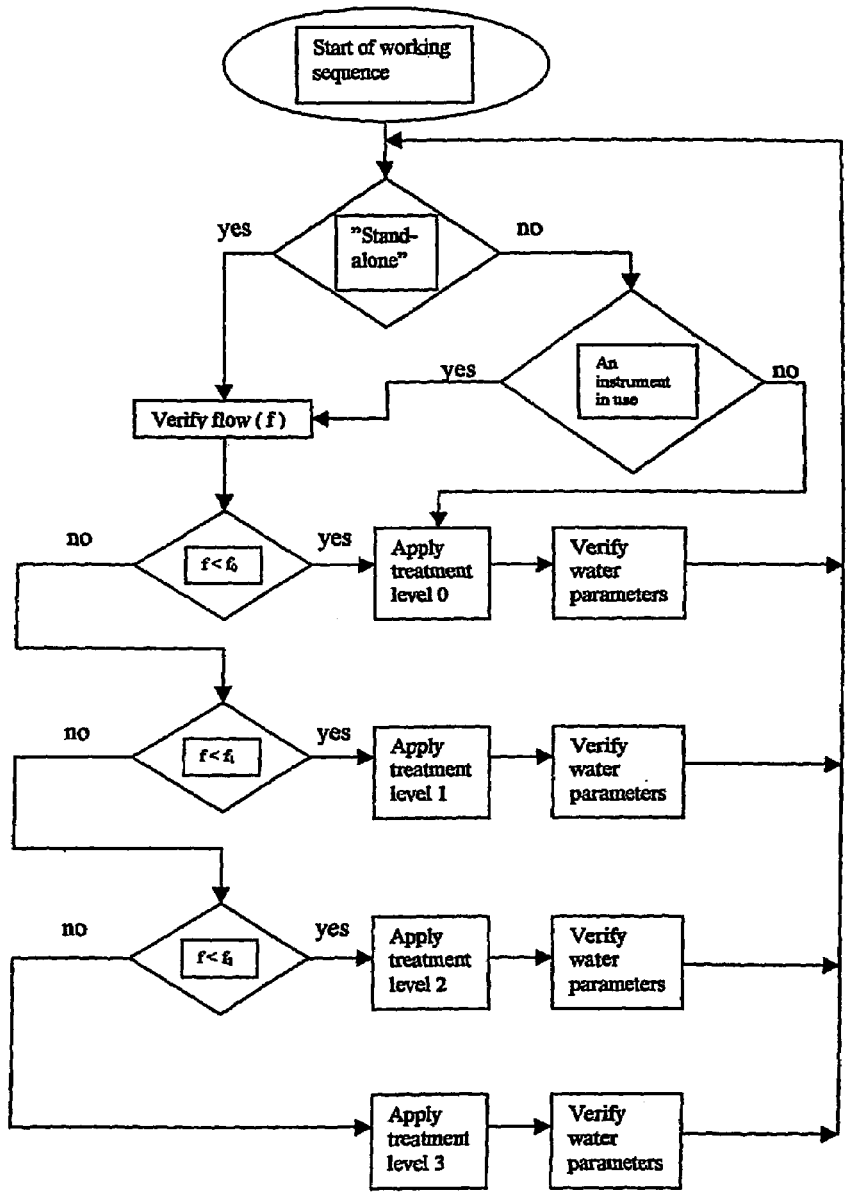

FIG. 3B shows a cleansing sequence that can be performed during use of the dental unit to which the device of the invention Is attached. In general terms, this sequence determines liquid flow through the water line in relation to an instrument In use, and, dependent upon the flow rate. Various different treatment levels, from no treatment at all to an extreme high level of treatment, can be selected, again each followed by a water parameter verification step to ensure that no fault has occurred in the system or the cleansing process. The level of the treatment applied may, if an electrochemical unit is used, relate to amount of time that the unit is on and the currents that are applied to It.

To ensure overall safety of the system the system is configured to shut down the water line and flow of liquid therethrough and prevent operation of the dental unit, if an error in operation is detected.

The invention claimed is:

1. A dental unit water line (DUWL) monitoring and maintenance apparatus, for monitoring a DUWL component of a dental unit, the apparatus comprising:
    cleansing means attached to the DUWL for cleansing the fluid passing therethrough;
    pumping means attached to the DUWL for pumping fluid in the DUWL;
    control means for controlling the cleansing means of the water line;
    monitoring means for monitoring the operation of the dental unit in use and storing data related to that operation; and
    a timer for timing and recording data relating to both periods of dental unit activity and inactivity, wherein, in use to control the overall cleansing procedures associated with both the dental unit and associated DUWL, the control means operates to receive data from the monitoring means and the timer and, based upon that data and reference data controls the cleansing means and operation of the pumping means.

2. An apparatus according to claim 1, wherein the monitoring means monitors the types of tools being used by the dentist and which are associated with the dental unit.

3. An apparatus according to claim 2, wherein the monitoring means provides data related to the duration of use of each of the tools.

4. An apparatus according to claim 1, wherein the control means controls the pumping means to operate automatically if it detects a certain period of inactivity by reference to the monitoring unit data and timer data.

5. An apparatus according to claim 1, wherein the control means monitors the operation of the cleansing unit to determine the level of any cleansing fluid being used by the cleansing means.

6. An apparatus according to claim 1, wherein the cleansing means comprise an electrochemical device and the control means monitors the output of the device to determine when electrodes associated with the device need replacement.

7. An apparatus according to claim 1, wherein the control means is configured to provide an audio or visual warning to the dentist should any feature of the dental unit be determined to be operating incorrectly or if it is determined that any specific non-routine maintenance procedure is requited.

8. An apparatus according to claim 1, wherein the control means is configured to prevent operation unless a certain sequence of maintenance procedures are first implemented by a user.

9. An apparatus according to claim 1, further comprising an ion exchange unit.

10. A dental unit water line (DUWL) monitoring and maintenance apparatus, for monitoring a DLTWL component of a dental unit, the apparatus comprising:
cleansing means attached to the DUWL for cleansing the fluid passing therethrough;
pumping means attached to the DUWL for pumping fluid in the DUWL;
control means for controlling the cleansing means of the water line;
monitoring means for monitoring the operation of the dental unit in use and storing data related to that operation, wherein the monitoring means monitors the types of tools being used by the dentist and which are associated with the dental unit; and
a timer for timing and recording data relating to both periods of dental unit activity and inactivity, wherein, in use to control the overall cleansing procedures associated with both the dental unit and associated DUWL, the control means operates to receive data from the monitoring means and the timer and, based upon that data and reference data controls the cleansing means and operation of the pumping means.

11. An apparatus according to claim 10, wherein the monitoring means provides data related to the duration of use of each of the tools.

12. An apparatus according to claim 10, wherein the control means controls the pumping means to operate automatically if it detects a certain period of inactivity by reference to the monitoring unit data and timer data.

13. An apparatus according to claim 10, wherein the control means monitors the operation of the cleansing unit to determine the level of any cleansing fluid being used by the cleansing means.

14. An apparatus according to claim 10, wherein the cleansing means comprise an electrochemical device and the control means monitors the output of the device to determine when electrodes associated with the device need replacement.

15. An apparatus according to claim 10, wherein the control means is configured to provide an audio or visual warning to the dentist should any feature of the dental unit be determined to be operating incorrectly or if it is determined that any specific non-routine maintenance procedure is required.

16. An apparatus according to claim 10, wherein the control means is configured to prevent operation unless a certain sequence of maintenance procedures are first implemented by a user.

17. An apparatus according to claim 10, further comprising an ion exchange unit.

18. A dental unit water line (DUWL) monitoring and maintenance apparatus, for monitoring a DUWL component of a dental unit, the apparatus comprising:
cleansing means attached to the DIJWL for cleansing the fluid passing therethrough;
pumping means attached to the DUWL for pumping fluid in the DUWL;
control means for controlling the cleansing means of the water line; monitoring means for monitoring the operation of the dental unit by a dental surgeon in use and storing data related to that operation, wherein the monitoring means monitors the types of tools being used by the dentist and which are associated with the dental unit and the monitoring means provides data related to the duration of use of each of the tools; and
a timer for timing and recording data relating to both periods of dental unit activity and inactivity, wherein, in use to control the overall cleansing procedures associated with both the dental unit and associated DUWL, the control means operates to receive data from the monitoring means and the timer and, based upon that data and reference data controls the operation of the pumping means to control flow of fluid through that DUWL.

19. An apparatus according to claim 18, further comprising an ion exchange unit.

20. An apparatus according to claim 18, wherein the cleansing means comprise an electrochemical device and the control means monitors the output of the device to determine when electrodes associated with the device need replacement.

* * * * *